US009022240B2

(12) United States Patent
Lewis

(10) Patent No.: US 9,022,240 B2
(45) **Date of Patent: *May 5, 2015**

(54) PRODUCTION OF POLIOVIRUS AT HIGH TITERS FOR VACCINE PRODUCTION

(71) Applicant: Crucell Holland B.V., Leiden (NL)

(72) Inventor: John A. Lewis, Little Compton, RI (US)

(73) Assignee: Crucell Holland B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/275,392

(22) Filed: May 12, 2014

(65) Prior Publication Data

US 2014/0242670 A1 Aug. 28, 2014

Related U.S. Application Data

(60) Continuation of application No. 13/660,412, filed on Oct. 25, 2012, now abandoned, which is a division of application No. 12/804,242, filed on Jul. 16, 2010, now Pat. No. 8,546,123.

(60) Provisional application No. 61/271,038, filed on Jul. 16, 2009.

(30) Foreign Application Priority Data

Jul. 16, 2009 (EP) .................................... 09165620

(51) Int. Cl.
*C12N 7/00* (2006.01)
*A61K 39/13* (2006.01)

(52) U.S. Cl.
CPC . *C12N 7/00* (2013.01); *A61K 39/13* (2013.01); *C12N 2770/32634* (2013.01); *C12N 2770/32651* (2013.01)

(58) Field of Classification Search
None
See application file for complete search history.

(56) References Cited

U.S. PATENT DOCUMENTS

| | | | |
|---|---|---|---|
| 4,525,349 | A | 6/1985 | Montagnon et al. |
| 5,994,128 | A | 11/1999 | Fallaux et al. |
| 6,544,424 | B1 | 4/2003 | Shevitz |
| 7,291,484 | B2 | 11/2007 | Yallop |
| 7,608,431 | B2 | 10/2009 | Yallop |
| 7,867,764 | B2 | 1/2011 | Pau et al. |
| 7,964,198 | B2 | 6/2011 | Pau et al. |
| 8,008,043 | B2 | 8/2011 | Yallop |
| 8,076,131 | B2 | 12/2011 | Vogels et al. |
| 8,097,453 | B2 | 1/2012 | Pau et al. |
| 8,227,243 | B2 | 7/2012 | Vogels et al. |
| 8,361,478 | B2 | 1/2013 | Pau et al. |
| 8,546,123 | B2 | 10/2013 | Lewis |
| 2006/0121611 | A1 | 6/2006 | Yallop |
| 2006/0240513 | A1 | 10/2006 | Yallop |
| 2007/0031932 | A1 | 2/2007 | Yallop |
| 2010/0144620 | A1 | 6/2010 | Van Den Nieuwenhof et al. |
| 2010/0311160 | A1 | 12/2010 | Yallop |
| 2011/0150930 | A1 | 6/2011 | Pau et al. |
| 2011/0311580 | A1 | 12/2011 | Vogels et al. |
| 2012/0014994 | A1 | 1/2012 | Pau et al. |
| 2012/0082694 | A1 | 4/2012 | Pau et al. |

FOREIGN PATENT DOCUMENTS

| | | | |
|---|---|---|---|
| CA | 2 763 091 | | 1/2011 |
| KR | 10 2012 70015 | | 4/2012 |
| WO | WO 97/00326 | | 1/1997 |
| WO | WO 01/38362 | A2 | 5/2001 |
| WO | WO 2005/095578 | A1 | 10/2005 |
| WO | WO 2007/007344 | A1 | 1/2007 |
| WO | WO 2011 006823 | A1 | 1/2011 |

OTHER PUBLICATIONS

Barrett PN, Mundt W, Kistner O, Howard MK. 2009. Vero cell platform in vaccine production: moving towards cell culture-based viral vaccines. Expert Rev. Vaccines 8: 607-618.

Bevilacqua JM, Young L, Chiu SW, Sparkes JD, Kreeftenberg JG. 1996. Rat immunogenicity assay of inactivated poliovirus. Dev. Biol. Stand. 86: 121-127.

Byrd P, Brown KW, Gallimore PH. 1982. Malignant transformation of human embryo retinoblasts by cloned adenovirus 12 Dna. Nature 298: 69-71.

Byrd PJ, Grand RJA, Gallimore PH. 1988. Differential transformation of primary human embryo retinal cells by adenovirus E1 regions and combinations of E1A + ras. Oncogene 2: 477-484.

Campbell SA, Lin J, Dobrikova EY, Gromeier M. 2005. Genetic determinants of cell type-specific poliovirus propagation in HEK 293 cells. J. Virol. 79: 6281-6290.

Card CJ, Smith T, Hunsaker B, Barnett B. 2005. Serum-free production of poliovirus: A comparative study using microcarriers, roller bottles and stationary cell culture. In: F. Gòdia and M. Fussenegger (Eds.), Animal Cell Technology meets Genomics, 761-765.

Doi Y, Abe S, Yamamoto H, Horie H, et al. 2001. Progress with inactivated poliovirus vaccines derived from the Sabin strains. In: Brown F (ed): Progress in Polio Eradication: Vaccine Strategies for the End Game. Dev. Biol. 105: 163-169.

Fallaux FJ, Bout A, van der Velde I, van den Wollenberg DJ, Hehir KM, Keegan J, et al. New helper cells and matched early region 1-deleted adenovirus vectors prevent generation of replication-competent adenoviruses. Hum Gene Ther Sep. 1, 1998;9(13):1909-17.

(Continued)

*Primary Examiner* — Stacy B Chen
(74) *Attorney, Agent, or Firm* — TraskBritt

(57) ABSTRACT

Described is a process for producing poliovirus, the process comprising: a) providing a serum-free suspension culture of cells, which are primary human retina (HER) cells that have been immortalized by expression of adenovirus E1 sequences, b) infecting the cells with poliovirus, at a cell density of between $2\times10^6$ cells/ml and $150\times10^6$ cells/ml, and c) harvesting poliovirus at a time of between 12 and 48 hours after infection.

33 Claims, 5 Drawing Sheets

(56) References Cited

OTHER PUBLICATIONS

Gallimore, P.H., Grand, R.J.A. And Byrd, P.J. (1986). Transformation of human embryo retinoblasts with simian virus 40, adenovirus and rasoncogenes. AntiCancer Res. 6, p. 499-508.
Jiang S, Pye D, Cox JC. 1986. Inactivation of poliovirus with β-propiolactone. J. Biol. Stand. 14: 103-109.
John J. 2009. Role of injectable and oral polio vaccines in polio eradication. Expert Rev. Vaccines 8: 5-8.
Kew OM, Sutter RW, de Gourville EM, Dowdle WR, Pallansch MA. 2005. Vaccine-derived polioviruses and the endgame strategy for global polio eradication. Annu. Rev. Microbiol. 59: 587-635.
Merten O.-W., Wu R, CouvéE, Crainic R. 1997. Evaluation of the serum-free medium MDSS2 for the production of poliovirus on Vero cells in bioreactors. Cytotechnology 25: 35-44.
Montagnon B, Vincent-Falquet JC, Fanget B. 1982. Thousand litre scale microcarrier culture of Vero cells for killed poliovirus vaccine. Promising results. Develop. Biol. Standard. 55: 37-42.
Montagnon BJ, Fanget B, Vincent-Falquet JC. 1984. Industrial-scale production of inactivated poliovirus vaccine prepared by culture of Vero cells on microcarrier. Rev. Infect. Dis. 6 (suppl. 2): S341-S344.
Pau et al., The human cell line PER.C6 provides a new manufacturing system for the production of influenza vaccines. Vaccine, 2001, pp. 2716-2721, vol. 16.
Furey et al., Bioprocessing —Scale-up of a Cell Culture Perfusion Process, Genetic Engineering News, Apr. 1, 2002, pp. 62-63, vol. 22, No. 7.
Thomassen et al., Platform Technology for Viral Vaccine Production: Comparison Between Attached and Suspension Vero Cells, Proceedings of the 21st Annual Meeting of the European Society for Animal Cell Technology (ESACT), Jun. 7-10, 2009, pp. 723-727.
Van Wezel AL, van Steenis G, Hannik CA, Cohen H. 1978. New approach to the production of concentrated and purified inactivated polio and rabies tissue culture vaccines. Develop. biol. Standard. 41: 159-168.
Wright PF, Modlin JF. 2008. The demise and rebirth of Polio—A modern Phoenix? J. Infect. Dis. 197: 335-336.
Yakovenko ML, Korotkova EA, Ivanova OE, Eremeeva TP et al. 2009. Evolution of the Sabin vaccine into pathogenic derivatives without appreciable changes in antigenic properties: need for improvement of current poliovirus surveillance. J. Virol. 83: 3402-3406.
Yallop C, Crowley J, Cote J, Hegmans-Brouwer K, Lagerwerf F, Gagne R, Martin JC, Oosterhuis N, Opstelten DJ, Bout A. Per.C6 cells for the manufacture of biopharmaceutical proteins. Modern Biopharmaceuticals—Design, Development and Optimization. vol. 3, 2005.
Berdichevsky et al., Establishment of Higher Passage PER.C6 Cells for Adenovirus Manufacture, Biotechnol. Prog., 2008, pp. 158-165, vol. 24.
Bjare, U., Propagation of Large Quantities of Poliovirus in Human Lymphoblastoid Cells Grown in a Serum-Free Medium, Journal of Virological Methods, 1984, pp. 259-268, vol. 9.
European Search Report for EP 09 16 5620 dated Jan. 11, 2010.
Fallaux et al., Characterization of 911: A New Helper Cell Line for the Titration and Propagation of Early Region 1-Deleted Adenoviral Vectors, Human Gene Therapy, Jan. 20, 1996, pp. 215-222, vol. 7.
Merten et al., Evaluation of the new serum-free medium (MDSS2) for the production of different biological: Use of various cell lies, Cytotechnology, 1994, pp. 47-59, vol. 14.
Declaration of Maria Grazia Pau submitted in U.S. Appl. No. 12/804,242 dated Jul. 11, 2013.
Declaration of Dr. Chris Yallop submitted in U.S. Appl. No. 12/804,242 dated Jul. 11, 2013.
Chinese Office Action for copending application No. 201080025614.2 with English Text of Second Office Action dated Aug. 13, 2013.
D1 English Translation of Zhao, Hui et al., "Optimal Cell Density and Multiplicity of Infection for Propagation of SARS-CoV in Vero Cells, Letters in Biotechnology," vol. 16, No. 3, pp. 274-275, May 31, 2005.
Bakker et al., Inactivated Polio Vaccine Development for Technology Transfer Using Attenuated Sabin Poliovirus Strains to Shift from Salk-IPV, Vaccine, 2011, pp. 7188-7196, vol. 29.
Barrett et al., Developing cell culture-derived pandemic vaccines, Current Opinion in Molecular Therapeutics, 2010, pp. 21-30, vol. 12, No. 1.
Deshpande et al., Detection of MEF-1 laboratory reference strain of poliovirus type 2 in children with poliomyelitis in India in 2002 & 2003, Indian J. Med Res., Dec. 2003, pp. 217-223, vol. 118.
Ferguson et al., Antigenic structure of poliovirus in inactivated vaccines, Journal of General Virology, 1993, pp. 685-690, vol. 74.
Genzel et al., Continuous cell lines as a production system for influenza vaccines, Expert Review of Vaccines, Dec. 2009, p. 1681, vol. 8, No. 12, Academic OneFile-Document, http://go.galegroup.com/ps/retrieve.do??sgHitCountType_None&sort=DA. . .
Henry et al., Insights Into Adenoviral Vector Production Kinetics in Acoustic Filter-Based Profusion Cultures, 2004, Biotechnology, Bioengineering, 2004, pp. 765-774, vol. 86, No. 7.
Houspie et al., Susceptibility of the PER.C6 cell line for infection with clinical human respiratory syncytial virus isolated, Journal of Virological Methods, 2012, pp. 37-41, vol. 81.
Kreeftenberg et al., Technology Transfer of Sabin-IPV to New Developing Country Markets, Biologicals, 2006, pp. 155-158, vol. 34.
Minor et al., Genetic and Antigenic Variation in Type 3 Polioviruses: Characterization of Strains by Monoclonal Antibodies and T1 Oligonucleotide Mapping, J. gen Virol., 1982, pp. 167-176, vol. 61.
Sanders et al., Per.C6® cells as a serum-free suspension cell platform for the production of high titer poliovirus: A potential low cost of goods option for world supply of inactivated poliovirus vaccine, Vaccine, 2012, http://dx.coi.org/10.1016/j.vaccine.2012.10.070.
Yokomizo et al., Rabies Virus Production in High Vero Cell Density Cultures on Macroporous Microcarriers, Biotechnol. Bioengineering, 2004, pp. 506-515, vol. 85, No. 5.
Ataei-Pirkooh et al., Poliovirus Particles do not Form in Preinfected Cells with Reovirus, Iranian Journal of Virology, 2009, pp. 23-28, vol. 3, No. 3.
Barral et al., MDA-5 Is Cleaved in Poliovirus-Infected Cells, Journal of Virology, Apr. 2007, pp. 3677-3684, vol. 81, No. 8.
Crucell report named "Evaluation of production of Sabin poliovirus strains on PER.C6 cells," at least as early as May 15, 2014.
Crucell report named "Experiment for growth kinetics polio virus at MOA 10," at least as early as May 15, 2014.
Crucell report named "Summary of Rat potency test summary for trivalent inactivated poliovirus vaccine prepared from poliovirus grown in PER.C6 cells," at least as early as May 15, 2014.
Crucell report named "Poliovirus production in PER.C6 cells at very high cell densities," at least as early as May 15, 2014.
Molla et al., Cell-Free, De Novo Synthesis of Poliovirus, Science, Dec. 13, 1991, pp. 1647-1651, vol. 254.
Paillet et al., Suspension-Vero cell cultures as a platform for viral vaccine production, Vaccine, 2009, pp. 6464-6467, vol. 27.
Sanders et al., PER.C6® cells as a serum-free suspension cell platform for the production of high titer poliovirus: A potential low cost of goods option for world supply of inactivated poliovirus vaccine, Vaccine, 2013, pp. 850-856, vol. 31.
Schirmer et al., Primary Clarification of Very High-Density Cell Culture Harvests By Enhanced Cell Settling, BioProcess Technical, Jan. 2010, pp. 32-39.
Toyoda et al., Oncolytic Treatment and Cure of Neuroblastoma by a Novel Attenuated Poliovirus in a Novel Poliovirus-Susceptible Animal Model, Cancer Res, 2007, www.aacrjournals.org, pp. 2857-2864, vol. 67, No. 6.
Zhao et al., Optimal Cell Density and Multiplicity of Infection for the Propagation of SARS-CoV in Vero Cells, Letters in Biotechnology, May 2005, (English Abstract), pp. 274-275, vol. 16, No. 3. [Entire English Translation Previously Submitted].
Liao et al., Optimal Conditions for Culture of Poliovirus in KMB17 Cells, Chin J. Biologicals, 2002, pp. 42-44, vol. 15, No. 1.

PRODUCTION OF POLIOVIRUS AT HIGH TITERS FOR VACCINE PRODUCTION

CROSS-REFERENCE TO RELATED APPLICATIONS

This application is a continuation of U.S. patent application Ser. No. 13/660,412, filed Oct. 25, 2012, now abandoned, which application is a divisional of U.S. patent application Ser. No. 12/804,242, filed Jul. 16, 2010, now U.S. Pat. No. 8,546,123, issued Oct. 1, 2013, which claims the benefit under 35 U.S.C. §119(e) of U.S. Provisional Patent Application Ser. No. 61/271,038, filed Jul. 16, 2009, and under 35 U.S.C. §119 of European Patent Application No. EP 09165620.7, filed Jul. 16, 2009, the disclosure of each of which is hereby incorporated herein in its entirety by this reference.

TECHNICAL FIELD

The disclosure relates to the field of cell culture and poliovirus production. More particularly, it concerns improved methods for the culturing of cells and production of poliovirus therefrom for the production of polio vaccines.

BACKGROUND

Polioviruses are members of the Enterovirus genus of the family Picornaviridae. Polioviruses are small, non-enveloped viruses with capsids enclosing a single stranded, positive sense RNA genome. There are three types of polioviruses: types 1, 2, and 3. Infections of susceptible individuals by poliovirus can result in paralytic poliomyelitis. Poliomyelitis is highly contagious. Two different polio vaccines have been developed, the inactivated poliovirus vaccine (IPV) of Salk and the live, attenuated oral poliovirus vaccine (OPV) of Sabin. Both vaccines are safe and effective. Each has its particular advantages and disadvantages, and both have played an important role in the control of poliomyelitis. For a review about polioviruses and polio vaccines see, e.g., Kew et al., 2005.

Oral polio vaccine (OPV) is cheap and convenient, and has been used massively. However, occasional recipients suffer from vaccine-associated paralytic poliomyelitis (VAPP) due to revertants in the vaccine. Furthermore, it has been observed in populations that have not been fully immunized that the attenuated Sabin polio strains have undergone sufficient mutational changes to cause outbreaks of paralytic disease that are clinically and epidemiologically indistinguishable from naturally occurring wild-type polio disease; these mutants are called circulating vaccine-derived polioviruses or cVDPVs (see, e.g., Kew et al., 2005; Wright and Modlin, 2008; Yakovenko et al., 2009).

There is a growing consensus that inactivated poliovirus vaccine (IPV) may contribute to more rapid eradication of wild-type polio and control of emergent cVDPV when used in conjunction with existing OPV strategies (Wright and Modlin, 2008; John, 2009).

However, production of IPV is more expensive (see, e.g., John, 2009) and may even be prohibitively expensive for less and least developed countries, where a strong need for polio vaccines still exists. The culture systems for producing bulk poliovirus material that can be used in a vaccine, in particular non-attenuated poliovirus, contribute to a large extent to the relatively high costs.

Propagation of poliovirus in HEK293 cells has been described as a system for the study of neuron-specific replication phenotypes of poliovirus, and it was described that attenuated forms of poliovirus, such as poliovirus containing point mutations in an IRES element as present in the Sabin strains, demonstrated reduced propagation in HEK293 cells (Campbell et al., 2005).

E1-immortalized human embryonic retina (HER) cells, in particular PER.C6® cells, have been described as suitable for propagation of various viruses, with an emphasis on influenza virus (Pau et al., 2001; WO 01/38362, the contents of which are incorporated herein by this reference). Although WO 01/38362 describes working examples of propagation of various strains of influenza virus, and of Herpes Simplex Virus (HSV) types 1 and 2, measles virus and rotavirus in PER.C6® cells, propagation of poliovirus was not exemplified in WO 01/38362. Furthermore, the conditions for replication of poliovirus in such cells have not been described, and cannot easily be predicted based on replication of unrelated viruses in these cells. Hence, it was hitherto unknown whether it would be feasible to economically produce poliovirus at industrial scale for vaccine production purposes in these cells.

For large-scale manufacturing of inactivated polio vaccines, poliovirus is generally propagated in Vero cells, which are monkey-derived. Vero cells are widely used for vaccine production, including inactivated as well as live attenuated polio vaccines, and thus far are the most widely accepted continuous cell lines by regulatory authorities for the manufacture of viral vaccines, and use of these cells for vaccine production is expected to rise by experts in the field (Barrett et al., 2009).

Large-scale microcarrier culture of Vero cells for inactivated poliovirus vaccine has been described by Montagnon et al., 1982 and 1984. A process for the large-scale production of a polio vaccine using Vero cells, and the resulting vaccine, are also described in U.S. Pat. No. 4,525,349, the contents of which are incorporated herein by this reference.

High titers of poliovirus (Sabin type 1) production (almost $2\times10^9$ $TCID_{50}$/ml) were described by (Merten et al., 1997) for conditions when Vero cells on microcarriers were cultured in serum-containing medium prior to the virus production phase in serum-free medium, but in view of the disadvantages of using serum these authors already indicate that a completely serum-free process is desired, and in such an optimized completely serum-free process these authors were able to obtain a titer of $6.3\times10^8$ $TCID_{50}$/ml.

Kreeftenberg et al (2006), involved in production of poliovirus for vaccine production at industrial scale, also mention yields of various wild type and Sabin strains of poliovirus in Vero cells grown on micro-carriers, which yields are similar for the different strains, the log titers being between 8.1 and 8.6. These authors also describe that the amount of virus needed to produce the final vaccine is significantly higher for IPV than for OPV, which results in a significantly higher production cost per dose for IPV than for OPV.

Serum-free production of poliovirus using Vero cells cultivated on microcarriers has also been described by (Card et al., 2005), and although the level of productivity was lower than in static cultures, the microcarrier cultures were described as easier in scale-up.

Despite the efficacy and industrial applicability of these microcarrier-based Vero cell cultures, the production of large quantities of poliovirus remains costly.

Production of poliovirus using suspension Vero cells has been described, resulting in lower virus titers ($^{10}\log$ $CCID_{50}$/ml between 6.5 and 7.9) than those observed in routine microcarrier Vero cells (van Eikenhorst et al., 2009).

DISCLOSURE

Here is demonstrated the very efficient propagation of poliovirus in E1-immortalized HER cells, wherein unprecedented high titers of poliovirus have been obtained. Obtaining such high titers, which provide a significant economic advantage over production of poliovirus in Vero cells, could not have been foreseen based on replication of other viruses in such cells. Neither could the conditions for an industrially feasible process be foreseen, since the conditions and obtainable advantages can vary widely for various different types of viruses that have vastly different properties.

Thus, provided is a process for the production of poliovirus, the process comprising the steps of: a) providing a serum-free suspension culture of cells, which are human fetal retina (HER) cells that have been immortalized by expression of adenovirus E1 sequences, b) infecting the cells with poliovirus, at a cell density of between $2\times10^6$ cells/ml and $150\times10^6$ cells/ml, and c) harvesting poliovirus at a time of between 12 and 48 hours after infection.

In certain embodiments, the cells are PER.C6® cells.

In certain embodiments, infecting is performed at a cell density of between about $5\times10^6$ cells/ml and $20\times10^6$ cells/ml, for instance, between about $8\times10^6$ cells/ml and $15\times10^6$ cells/ml, e.g., at about $10\times10^6$ cells/ml.

In certain embodiments, the harvesting of the poliovirus is performed at a time of between about 18 and 30 hours after infection, for instance, at about 24 hours after infection.

These conditions enable one to obtain very high titers (around $10^{10}$/ml, which is significantly more than 10 times the titers typically obtained using microcarrier based Vero cells for wild type polio strains) of poliovirus in a relatively short process, which therefore has significant economic advantages over the processes currently used for poliovirus production for vaccine preparation. This was demonstrated for all three types of poliovirus: type 1 (Brunenders strain), type 2 (MEF strain) and type 3 (Saukett strain).

In certain embodiments therefore, the poliovirus is wild-type virulent poliovirus, for instance, poliovirus type 1, poliovirus type 2 or poliovirus type 3. In certain embodiments, the poliovirus is poliovirus type 1 strain Mahoney or Brunenders, poliovirus type 2 strain MEF (or MEF-1), or poliovirus type 3 strain Saukett. In other embodiments, the poliovirus is an attenuated poliovirus (being less neurovirulent), for instance, a Sabin strain (which can also be of type 1, 2 or 3).

Further provided is a process for producing a polio vaccine, comprising a process for producing poliovirus according to the invention, further comprising purifying, optionally inactivating, and formulating the harvested poliovirus to obtain a polio vaccine. For an IPV, inactivation by formalin or other means is performed. For an OPV, the step of inactivating is not required.

Also provided is a poliovirus bulk useful for preparation of a polio vaccine, the bulk being obtainable by a process for producing poliovirus and comprising culture medium and a poliovirus titer of at least $10^{9.4}$ $CCID_{50}$/ml, for instance, between about $10^{9.5}$ and $10^{11}$ $CCID_{50}$/ml, for instance, between about $10^{9.8}$ and $10^{10.8}$ $CCID_{50}$/ml. In certain embodiments, the bulk has a volume of between 1 and 1000 liters. In further embodiments, the bulk contains cells and/or cell debris, of cells used according to the processes of the invention. In certain embodiments, the bulk is present in a bioreactor. In other embodiments, the bulk has been removed from the bioreactor and is present in a suitable container.

In another aspect, provided is poliovirus and polio vaccine obtainable according to methods hereof. The poliovirus and/or the vaccine is free of monkey proteins, preferably free of non-human proteins. It will also be free of other non-human host cell residuals. In contrast, poliovirus that has been produced according to conventional methods will contain residual non-human protein and/or other non-human residuals, from the host cells used and/or from the serum used during cell culture. Thus, poliovirus produced according to the disclosure suffers from less contamination of non-human impurities resulting from the production process than poliovirus produced using conventional processes.

Also provided is a process for obtaining a poliovirus preparation in cell culture at a titer of at least about $10^{9.4}$, preferably at least $10^{9.8}$, more preferably at least $10^{10}$, for instance, between $10^{10.5}$ and $10^{11}$ $CCID_{50}$/ml, comprising the steps of: a) providing a serum-free suspension culture of cells, which are human fetal retina (HER) cells that have been immortalized by expression of adenovirus E1 sequences, b) infecting the cells with poliovirus, at a cell density of between $2\times10^6$ cells/ml and $150\times10^6$ cells/ml, and c) harvesting poliovirus at a time of between 12 and 48 hours after infection to obtain the poliovirus preparation having the concentration. Preferred embodiments are the same as described above for the process for the production of poliovirus according.

Provided are suitable processes that can be used for large-scale and economic production of polioviruses for use in vaccines. This may aid in providing access to affordable polio vaccine in developing countries on a sustainable basis.

DETAILED DESCRIPTION

Figure 1:
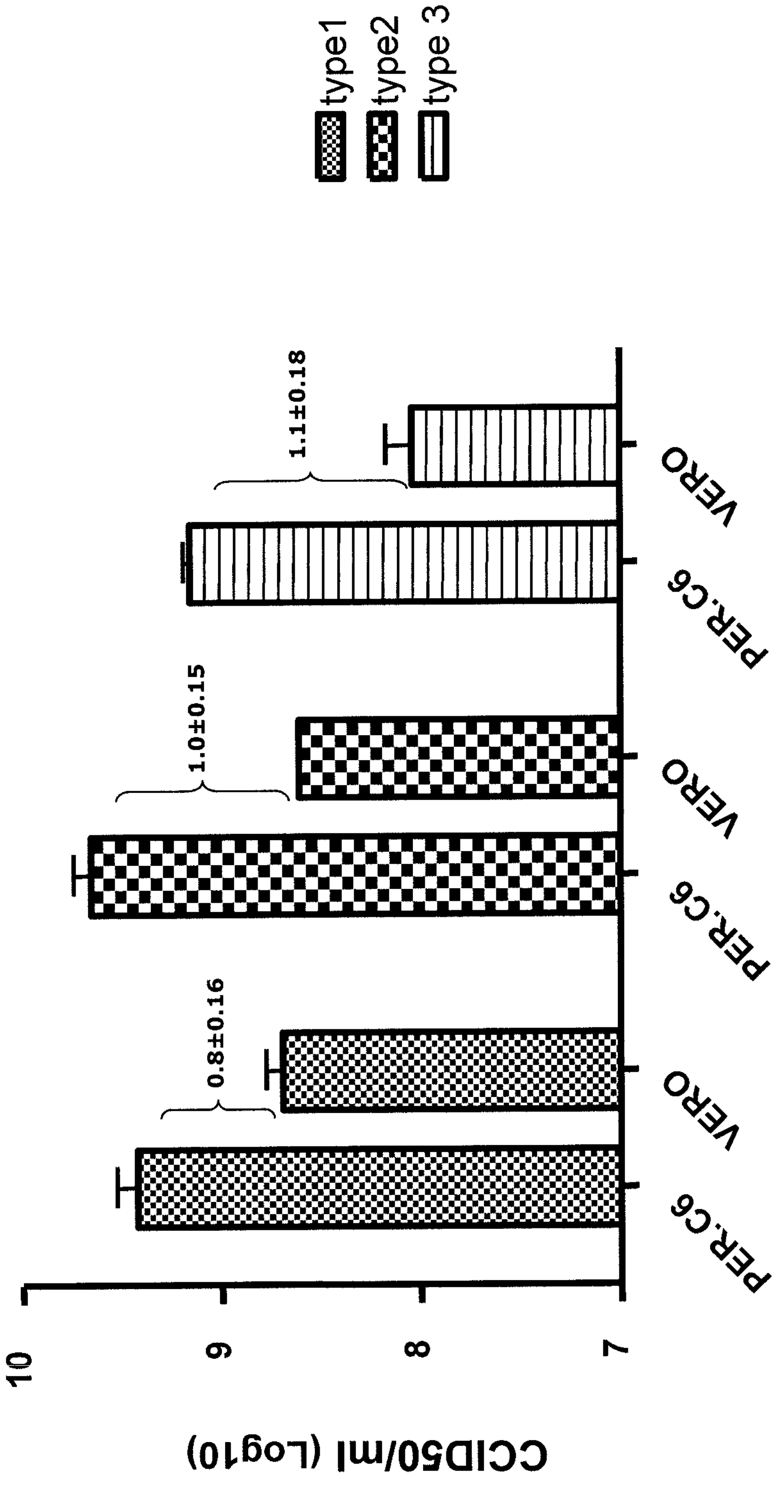
FIG. 1. Production of poliovirus in adherent PER.C6® and Vero cells.

The cells used herein are primary human retina (in the art often referred to as "HER") cells that have been immortalized by expression of adenovirus E1 sequences. They are derived from human primary retina cells, and selection for immortalization is provided by the adenoviral E1A and E1B transforming activity. Immortalization of HER cells with adenoviral E1 sequences, and cells that can be used in the processes according to the invention, have, for instance, been described in U.S. Pat. No. 5,994,128, in (Byrd et al., 1982, 1988), and (Gallimore et al., 1986). Primary HER cells can be isolated from fetuses (Byrd et al., 1982, 1988). Immortalized cells are also known as continuous cell lines in the art, and have the potential for an infinite lifespan (see, e.g., Barrett et al., 2009). In a preferred aspect, the cells used in the processes hereof are PER.C6® cells. PER.C6® cells for the purpose of the present application shall mean cells from an upstream or downstream passage or a descendent of an upstream or downstream passage of cells as deposited under ECACC no. 96022940 on Feb. 29, 1996. PER.C6® cells are described in U.S. Pat. No. 5,994,128, the contents of which are incorporated herein by this reference, and in (Fallaux et al., 1998). These cells are very suitable for influenza virus production to produce cell-based influenza vaccines, since they can be infected and propagate the virus with high efficiency, as, for instance, described in (Pau et al., 2001) and WO 01/38362. PER.C6® cells are capable of growing in suspension in the absence of serum, as, for instance, described in (Yallop et al., 2005). It is demonstrated herein that these cells are also very suitable for production of poliovirus to high levels in serum-free suspension cultures.

Moreover, the conditions employed are economically and regulatory advantageous.

The use of microcarriers is not required for the instant invention, in contrast to the widely used processes with Vero cells. Microcarriers contribute to high costs of poliovirus produced using the conventional Vero cell based processes.

Serum free according to the invention means that the medium used for cell growth and infection lacks whole serum as an ingredient. It may not be entirely free of serum-derived products such as, for example, bovine serum albumin (BSA), however, in preferred embodiments such components are also not present, or have been recombinantly produced in the absence of any animal derived components. In preferred embodiments, the complete method is carried out in the absence of any components that have been directly derived from animals, such as serum or serum-components, etc. In a preferred embodiment the method of producing a vaccine is performed in animal component free conditions. This means that the medium used for cell growth and infection is devoid of any animal derived components. Moreover, any additives supplemented to the medium during the process of vaccine production are also free of animal-derived components. The absence of animal components in the process of making the polio vaccine offers a process that is more controlled and safe. For this reason, PER.C6® cells, which are fully characterized human cells and which were developed in compliance with GLP/GMP are very well suited for the use in vaccine manufacturing. Different culture media can be used, and choosing the optimal culture medium for the cells and circumstances used is part of the routine tasks of the skilled person in this field. Suitable culture media for the purpose of the invention are thus well known to the skilled person and can generally be obtained from commercial sources in large quantities, or custom-made according to standard protocols. Culturing can be done, for instance, in dishes, roller bottles or in bioreactors, using batch, fed-batch, continuous systems and the like. In order to achieve large scale (continuous) production of virus through cell culture it is preferred in the art to have cells capable of growing in suspension, and it is preferred to have cells capable of being cultured in the absence of animal- or human-derived serum or animal- or human-derived serum components. Suitable conditions for culturing cells are known (see, e.g., Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9). Serum-free culture media that can be used according to the processes of the invention include but are not limited to standard media that can be ordered from the catalogs of media vendors, including CDM4PERMAb™ (Thermo Scientific HyClone, cat. nos. SH30871, SH30872). Further, custom-ordered media such as Permexcis (Lonza) are suitable. Examples of other serum-free media that may be suitable for use in the processes of the invention are AEM (Invitrogen, cat. no. 12582-011), EX-CELL™ VPRO medium (JRH Biosciences, catalog number 14561) and CDM4Retino™ (HyClone, cat. nos. SH30520, SH30519).

In certain optional and non-limiting embodiments, it is possible to supplement the serum-free media in the processes of the invention with lipids and/or hydrolysates and/or other supplements, to further improve productivity.

The term "about" for numerical values as used in the present disclosure means the value±10%.

Infecting the cells with poliovirus and/or virus propagation in the processes according to the invention is, for instance, suitably performed at a temperature of between about 33° C. and 38° C. In preferred embodiments, the infecting and/or virus propagation is performed at a temperature of between about 34° C. and 36° C., in certain embodiments between about 34.5° C. and 35.5° C., e.g., at about 35° C.

Infecting the cells with poliovirus in the processes according to the invention can, for instance, be suitably done at a multiplicity of infection (MOI) of between 0.001 and 10. In certain embodiments, the infecting is performed at an MOI of between about 1 and 3, for instance, at an MOI of about 2. Infecting at such a relatively high MOI (>0.1, preferably about 1 or higher) may further augment the high efficiency, high yielding process.

As described herein, the cells are infected with poliovirus, preferably at a high cell density. In certain aspects the infection with poliovirus takes place when the cells have a density of between $1\times10^6$ cells/ml and $150\times10^6$ cells/ml, preferably of between $2\times10^6$ cells/ml and $150\times10^6$ cells/ml. In certain preferred embodiments, the infecting is performed at a cell density of between about $5\times10^6$ cells/ml and $20\times10^6$ cells/ml, for instance, between about $8\times10^6$ cells/ml and $15\times10^6$ cells/ml, for instance, at about $10\times10^6$ cells/ml. As far as the inventor hereof is aware, the processes hereof provide the highest cell concentrations at which non-adenoviral virus vaccines are manufactured. Advantages of these processes are that very high titers of poliovirus can be obtained, i.e., at least an order of magnitude higher than with the conventional Vero processes of the prior art.

In the processes described herein, the poliovirus is harvested at a time of between 12 and 48 hours after infection. In certain embodiments, the harvesting of the poliovirus is performed at a time of between about 18 and 30 hours after infection, for instance, between about 20 and 28 hours, between about 22 and 26 hours after infection, e.g., at about 24 hours after infection. Thus, the processes according to the invention can be used to obtain the high titers of poliovirus extremely fast, which also helps in making the processes of the invention economically extremely attractive compared to the much longer processes that are conventional in the art.

Most large-scale suspension cultures are operated as batch or fed-batch processes because they are the most straightforward to operate and scale up, and such processes are in principle suitable for the processes of the instant invention. However, continuous processes based on perfusion principles are becoming more common. In certain embodiments of the invention the producer cells are cultured in a perfusion system.

Batch, fed-batch, perfusion, and perfusion production processes have been used with PER.C6® cells, e.g., for recombinant antibody production. In batch cultures, viable cell concentration greater than $12\times10^6$ cells/ml are routinely achieved. Viable cell concentration up to $40\times10^6$ cells/ml have been demonstrated multiple times using fed batch. In perfusion processes, peak cell concentrations over $150\times10^6$ cells/ml are routinely achieved (Kral et al., 2009).

"Perfusion culturing of cells" has its conventional meaning in the art, i.e., it means that during culturing cells are retained by a separation device in which there is an outflow of liquid having a lower cell density than prior to separation and in which there is an inflow of cell culture medium. The use of perfused culture is in response to the challenge of growing cells at high densities (e.g., 10-$50\times10^6$ viable cells/mL). In order to increase densities, the medium is constantly, or intermittently, replaced with a fresh supply in order to make up for nutritional deficiencies and to remove toxic products. Perfusion also allows for a better control of the culture environment (pH, $dO_2$, nutrient levels, etc.). Perfusion of fresh medium through the culture can be achieved by retaining the cells with a variety of separation devices (e.g., fine mesh spin filter, hollow fiber or flat plate membrane filters, settling tubes). In certain embodiments, the separation device is a filter module comprising hollow fibers, i.e., tubular membranes. The internal diameter of the tube is usually between 0.3 and 6.0 mm, for instance, between 0.5 and 2.0 mm. In certain embodiments, the mesh size (pore size) in the membrane is chosen such that the size of the pores in the mesh is close to the diameter of the cells, ensuring a high retention of cells while cell debris can pass the filter. In other embodiments, the mesh size is significantly smaller than the diameter of the cells. Preferably, the mesh size is between 0.1-30 μm, e.g., between 0.1 and 3 μm, e.g., about 0.2 μm. Filter modules comprising hollow fibers are commercially available from, for example, General Electric (formerly Amersham).

Perfusion is used in order to maintain desired levels of certain metabolites and to remove and thereby reduce impurities in the culture medium. Typically, perfusion is not carried out at all times during culturing and is generally carried out only from time to time during culturing as desired. For example, perfusion is not typically initiated until after certain media components such as glucose begin to become exhausted and need to be replaced.

Several perfusion systems are known and are in principle suitable for use herein. With the term "perfusion system" is meant the combination of a bioreactor connected to a separation device. The separation device can either be incorporated in the bioreactor (e.g., fine mesh spin filter) or remain outside the bioreactor (e.g., hollow fiber). In both cases, as previously explained, the separation device prevents washout of the cell mass from the reactor and enables medium refreshment. The bioreactors may be operated with (connected to) an alternating tangential flow (ATF) perfusion system (e.g., ATF System, Refine Technology, Co., East Hanover, N.J.). Tangential flow can be achieved according to methods known to the person skilled in the art and as described in, e.g., in U.S. Pat. No. 6,544,424, the contents of which are incorporated herein by this reference. Operation of the ATF perfusion system has been described, and is scalable (Furey, 2002). ATF systems allow the cells to be cultured for a longer period of time and to reach high cell densities without having a blocked filter. Indeed, extremely high cell densities of over $100\times10^6$ viable cells/mL can be obtained with the use of an ATF perfusion system, e.g., with PER.C6® cells (see, e.g., Yallop et al., 2005 and WO 2005/095578, the contents of which are incorporated herein by this reference). However, in those earlier reports, the PER.C6® cells in perfusion systems were used for recombinant production of antibodies, i.e., a completely different purpose, and not infected with poliovirus.

In certain embodiments, perfusion with, for example, an ATF system is advantageous during the preculture phase (i.e., before infection with poliovirus), since it allows obtaining very high cell densities, and the cells are in good condition for subsequent infection with poliovirus. In order to reach the high cell densities, the culture medium is in certain embodiments at least partially perfused during a portion of time during cell growth. In certain embodiments, perfusion is started once a cell density between about $2\times10^6$ viable cells/mL and $8\times10^6$ viable cells/mL is reached.

In the processes hereof, cells are infected with poliovirus. Typically, the virus will be exposed to the appropriate producer cell under optimal conditions, permitting uptake of the virus. A person skilled in the art knows how to find the optimal further conditions, i.e., for agitation, pH, dissolved oxygen ($dO_2$ or DO). Usually, the optimal agitation is between about 50 and 300 rpm, typically about 100-200, e.g., about 150, typical DO is 5-60%, the optimal pH is between 6.7 and 7.7. Typically, poliovirus infects the cells of the invention spontaneously, and bringing the cells into contact with poliovirus particles is sufficient for infection of the cells. Generally, a poliovirus seed stock is added to the culture to initiate infection, and subsequently the poliovirus propagates in the cells.

It was advantageously possible to infect a cell culture according to the invention with poliovirus at high cell densities, i.e., around $10\times10^6$ cells/mL, and very high titers (higher than $10^{10}$ $CCID_{50}$/ml) of poliovirus were obtained.

In certain embodiments, the viability of the cell culture prior to infection remains higher than 75%, meaning that at least 75% of the total amount of cells in the culture is viable at the moment of infection. In certain embodiments, the viability of the cell culture at infection is at least 80%, in further embodiments at least 85%. Viability can be measured using routine methods available to the skilled person, e.g., trypan blue exclusion, Casy cell count, and the like.

In certain embodiments, the cell density at infection is between about $10\times10^6$ and $50\times10^6$ viable cells/mL, e.g., between about $10\times10^6$ and $20\times10^6$ viable cells/mL, e.g., between about $10\times10^6$ and $15\times10^6$ viable cells/mL. These cell densities allow for high virus productivity with limited accumulation of cell debris and host cell DNA, which gives an advantage of these embodiments in downstream processing of the poliovirus harvest. Thus, provided is an optimized process for poliovirus production, yielding high titers of poliovirus, while at the same time providing a harvest material that is still manageable for downstream processing purposes.

In other embodiments, the cell density at infection is between about $15\times10^6$ and $150\times10^6$ cells/mL, e.g., between about $15\times10^6$ and $80\times10^6$ cells/mL, e.g., between about $20\times10^6$ and $50\times10^6$ cells/mL. Infections at these cell densities may produce even higher concentrations of virus.

In certain embodiments hereof, a method is provided for producing poliovirus bulk at a titer of at least $10^{10}$ $CCID_{50}$/ml.

The titer is expressed as $CCID_{50}$, which is 50% of the cell culture infective dose. This is sometimes also referred to as $TCID_{50}$ (50% of tissue culture infective dose), but since it is determined by cell culture, the term $CCID_{50}$ is used herein.

The virus is placed in contact with the cells to allow the virus to infect the cells and to propagate. For instance, the viral seed lot is added to the cell culture and allowed to absorb on the cells, for instance, for about 30 minutes at gentle stirring (e.g., about 30 rpm), after which further culture medium may be added and the pH adjusted if desired, stirring speed may be adjusted and the culture maintained. After the infection step, amplification of the number of virus particles takes place. Of course, also this step is preferably performed in PER.C6® cells that are cultured in suspension in the absence of serum, and more preferably under conditions that are completely free of components directly derived from animals. This step can suitably be performed in bioreactors, for instance, at scales of between 1 and 20,000 liters, e.g., between 10 and 2,000 liters, e.g., between 50 and 1,000 liters, which scale can easily be adjusted to the demand for the vaccine. In certain embodiments, the bioreactor is a single use bioreactor (SUB).

After propagation of the poliovirus in the cells, the virus or components thereof are harvested from the cell culture. This can be done by routine methods, which are as such known to the skilled person. The virus produced and released in the cell culture medium can be separated from the cellular biomass by conventional methods, such as centrifugation or ultrafiltration, and harvested in the supernatant. In such a case the centrifugation or filtration is the harvesting step. Conventional processes for harvesting the virus can be used, for instance, those described in U.S. Pat. No. 4,525,349. In brief, the liquid medium suspension containing the virus is typically withdrawn, filtered and concentrated by, for instance, ultrafiltration. For instance, at the end of the culture, harvesting is carried out by collecting the culture medium containing the viral suspension. The harvest can be filtered, for instance, using a 0.22 μm filter, and optionally stored at 4° C.

The filtered harvest can optionally be ultrafiltrated to concentrate the viral suspension, and subsequently, the poliovirus can be purified, e.g., using gel filtration and/or ion exchange chromatography, for instance, following the procedures as described in U.S. Pat. No. 4,525,349, the contents of which are incorporated herein by this reference, or in Van Wezel et al., (1978). The resulting concentrated virus suspension can optionally be diluted, and for preparing IPV the poliovirus therein will be inactivated, for which conventional methods can be used.

Methods for harvesting and purifying poliovirus or viral components, and production of vaccines therefrom are used in the art for decades already, and thus are well known and have been amply described, for example, in (Van Wezel et al., 1978; Montagnon et al., 1984; WO 2007/007344; U.S. Pat. No. 4,525,349), all incorporated by reference herein.

Polio vaccines are based on live virus or inactivated virus. They contain the poliovirus D-antigen, which is the important protective antigen. Virus yields can be measured by standard virus titration techniques, while the determination of the D-antigen concentration is also performed by routine techniques well known to the skilled person, e.g., the D-antigen ELISA assay. Immunogenicity can, for instance, be determined by in vivo testing in animals. Potency can be determined using the D-antigen ELISA and by a poliovirus neutralizing cell culture assay on sera from previously immunized rats.

In general, each of the poliovirus strains is cultured in a separate process, and if, for instance, a trivalent vaccine containing three types of poliovirus is prepared, the (inactivated, for IPV) viruses are mixed and formulated for preparation of individual dosages. In certain embodiments, for example, a final vaccine per dose (e.g., 0.5 ml) may, for instance, comprise 40 D-antigen units (DU) of type 1 poliovirus, 8 DU of type 2 poliovirus and 32 DU of type 3 poliovirus, determined by comparison to reference preparations.

Inactivation of poliovirus can be done according to methods known in the art, e.g., with formalin or with β-propiolactone (BPL) (see, e.g., Jiang et al., 1986). In certain embodiments, inactivation is performed with formalin, for instance, by the following method: the purified viral suspension is filtered over a 0.22 μm membrane, heating to 37° C. with steady magnetic stirring for 24 hours, after which a formol solution is added to achieve a concentration of 1 per 4,000. While keeping the viral suspension at 37° C., the magnetic stirring is continued for the first four days. On the sixth day, the viral suspension is filtered over a 0.22 micron membrane, and inactivation is continued under suspension at 37° C. until the twelfth day. The inactivated viral suspension is homogenized and may be stored, e.g., at 4° C. After this step, concentrated and/or final batches for administration may be prepared, for instance, by mixing the desired preparations.

In certain embodiments, the purified poliovirus or viral component is formulated into a pharmaceutical composition. This can be done according to a variety of methods and using a variety of buffers all according to routine methods well known to the person skilled in the art after reviewing the instant disclosure. In general, it entails bringing the poliovirus particles in a pharmaceutically acceptable composition, comprising the poliovirus and at least a pharmaceutically acceptable excipient. Such a composition may be prepared under conditions known to the skilled person, and in certain embodiments is suitable for administration to humans. In certain embodiments, the composition may comprise buffered culture medium, which may optionally be Medium M-199, which is used as formulation buffer for certain registered conventional inactivated poliovirus vaccines. Further, phosphate buffered saline may be used, and the final dosage formulations may comprise, for instance, 0.5% of 2-phenoxyethanol and a maximum of 0.02% of formaldehyde per dose as antimicrobial preservatives.

Pharmaceutically acceptable carriers or excipients and diluents are well known in the art and used extensively in a wide range of therapeutic products. Preferably, carriers are applied that work well in vaccines. In certain embodiments, the vaccines further comprise an adjuvant, e.g., alum. Adjuvants are known in the art to further increase the immune response to an applied antigenic determinant.

For administering to humans, the invention may employ pharmaceutical compositions comprising the poliovirus and a pharmaceutically acceptable carrier or excipient. In the present context, the term "Pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)). The purified inactivated poliovirus or immunogenic parts thereof preferably are formulated and administered as a sterile solution. Sterile solutions may be prepared by, e.g., sterile filtration or by other methods known in the art. The solutions are then lyophilized or filled into pharmaceutical dosage containers. The pH of the solution generally is in the range of pH 3.0 to 9.5, e.g., pH 5.0 to 7.5. The poliovirus or immunogenic parts thereof typically are in a solution having a suitable pharmaceutically acceptable buffer, and the solution of poliovirus may also contain a salt. Optionally stabilizing agent may be present, such as albumin. In certain embodiments, detergent is added. In certain embodiments, the vaccine may be formulated into an injectable preparation. These formulations contain effective amounts of poliovirus or immunogenic parts thereof, are either sterile liquid solutions, liquid suspensions or lyophilized versions and optionally contain stabilizers or excipients.

A polio vaccine can be monovalent, containing one type of poliovirus (type 1, 2 or 3), or divalent (containing two types of poliovirus, e.g., types 1 and 2, 1 and 3 or 2 and 3), or trivalent (containing three types of poliovirus, i.e., types 1, 2 and 3).

It is possible to produce IPV from wild-type polioviruses. Alternatively, IPV may be produced from non-virulent live poliovirus, e.g., from the Sabin strains, which would further reduce the risk of reintroducing wild-type poliovirus from IPV manufacturing (see, e.g., WO 2007/007344, the contents of which are incorporated herein by this reference, and Doi et al., 2001). The process is suitable for production of wild-type poliovirus (types 1, 2 and 3, e.g., the type 1 strain Mahoney, type 2 strain MEF, or type 3 strain Saukett) as well as of non-virulent types of poliovirus (e.g., the Sabin strains). The process can thus be used to produce poliovirus for IPV, as well as for OPV. The processes hereof applied to produce IPV may serve to drive the cost down to such an extent that IPV may become available to less and least developed countries. Although in general OPV is cheaper than IPV when prepared according to conventional methods, the highly efficient processes of the invention can still reduce the costs of the bulk material for OPV and hence reduce the costs thereof as well.

The administration of a polio vaccine can, for instance, be performed intramuscularly, intradermally, or orally, according to methods known in the art.

The poliovirus vaccine obtainable according to the invention can be used as a stand-alone vaccine, but in other embodiments can be combined with other vaccines in the regular manner, e.g., in the form of a combined vaccine against diphtheria, pertussis, tetanus and polio, and can optionally include further vaccine components, e.g., against hepatitis B and/or heamophilus influenzae, etc. Thus, the poliovirus is suitable for use in the expanded program on immunization (EPI), and can be combined with the vaccines in that program. Similarly to conventional poliovirus vaccines, the vaccine according to the invention can be given as a single dose, or preferably in prime-boost regimens wherein multiple doses of vaccine are administered with appropriate time intervals, e.g., two injections at a 1-2 month time interval, followed by a booster dose 6-12 months later; or, for instance, an initial oral dose, followed by a second dose about 8 weeks later and a third dose 8-12 months after the second dose; or, for instance, for infants a first oral dose at 6-12 weeks of age, followed by a second dose about 8 weeks after the first dose and a third dose at about 6-18 months of age; or, for example, only a single dose for previously vaccinated persons at increased risk; etc. The optimal dosage regime can be determined according to standard medical practice and will generally follow the same schemes as those for the available poliovirus vaccines.

The invention is further described with the aid of the following illustrative Examples.

EXAMPLES

Example 1

Efficient Production of Poliovirus on Adherent PER.C6® Cells

To test propagation of poliovirus on adherent PER.C6® cells and generate virus stocks, poliovirus type 1 (Brunenders), type 2 (MEF-1) and type 3 (Sauckett), were obtained from SBL (Sweden). Titers of these stocks, each produced on Vero cells, were around $10^6$ $CCID_{50}$/ml. PER.C6® cells (Fallaux et al., 1998) were grown in culture medium (DMEM with 10% FBS and 10 mM $MgCl_2$). Three T175 flasks were seeded with $30\times10^6$ PER.C6® cells/flask in 25 ml culture medium for each type of poliovirus and inoculated the next day with a multiplicity of infection (MOI) of 0.1 (0.1 $CCID_{50}$/cell) at 37° C. and 10% $CO_2$ in a humidified incubator. Three days later, cells and medium were harvested and crude lysates were prepared by two freeze/thaw cycles. Following centrifugation to remove the cell debris, supernatants were divided in aliquots and stored at −80° C. In parallel, one T175 flask was seeded with $6.25\times10^6$ Vero cells in 25 ml Vero cell culture medium (Optipro SFM medium supplemented with 4 mM L-glutamine) for each strain of poliovirus and infected with the same MOIs. The Vero cultures were also harvested after 3 days, freeze/thawed twice and aliquotted for storage.

Production of poliovirus was then quantified by a $CCID_{50}$ assay using Vero cells. Hereto, $1.25\times10^4$ Vero cells were seeded in each well of a 96-well plate in 100 μl medium and incubated at 37° C. and 5% $CO_2$. The next day, a series of 15 five-fold dilutions of the poliovirus samples were prepared in Vero cell culture medium and 100 μl of the dilutions number 5 to 15 were added to column 1 to 11 in the 96-well plate in eight-fold. Column 12 served as an uninfected control column. Seven days later the wells were analyzed for occurrence of cytopathogenic effect (CPE) and titers were calculated using the Spearman-Karber method:

$$\text{Endpoint titer}(\log_{10})=X_o-d/2+d/n*\Sigma X_i$$

Where $X_o$ is the $\log_{10}$ value of the highest dilution at which all inoculations are still positive, d is the $\log_{10}$ value of the dilution factor used, n is the number of replicates at each dilution and $\Sigma X_i$ is the sum of all wells that are positive including dilution $X_o$.

The results of the titration experiment are depicted in FIG. 1 and show that on adherent PER.C6® cells the titers were >5 times higher than on Vero cells for type 1 poliovirus and >10 times higher in case of type 2 and 3. Differences in production of virus particles per cell are expected to be smaller since more PER.C6® cells were seeded. For both PER.C6® and Vero cells, the confluence of the cell monolayer was estimated to be ~80%.

From these experiments it was concluded that production of poliovirus on adherent monolayers of PER.C6® cells was at least as good as on Vero cells.

Example 2

Efficient Production of Poliovirus in PER.C6® Cells in Suspension

To investigate the propagation of poliovirus on PER.C6® cells in suspension, small scale experiments were performed to test different culture media, multiplicity of infections (MOI) and time of harvest (TOH). Hereto, PER.C6® cells were cultured in three different media: AEM (Invitrogen), BMIVg (commercially available as Permexcis™, from Lonza) and CDM4PERMAb (Hyclone). On the day of infection, cells cultured in one type of medium were counted and reseeded in the same type of medium at different cell densities (1.5, 2.5, 3.5 or 5 million cells/ml) and infected with different MOIs (0.01, 0.05 or 0.1 $CCID_{50}$/cell) at 37° C. in a humidified incubator on a shaking platform. The platform (IKA KS 260) had a 10 mm orbital diameter and was used at 100 rpm for 125 or 250 ml shake flasks filled with 15-20 ml medium. For AEM medium, cells were seeded at 1.5 or 2.5 million cells/ml since AEM did not support higher cell densities. In this way multiple cultures were prepared that were harvested 2, 3 or 4 days after infection. All samples were freeze/thawed twice and kept at −20° C. or less until further analysis.

Figure 2:
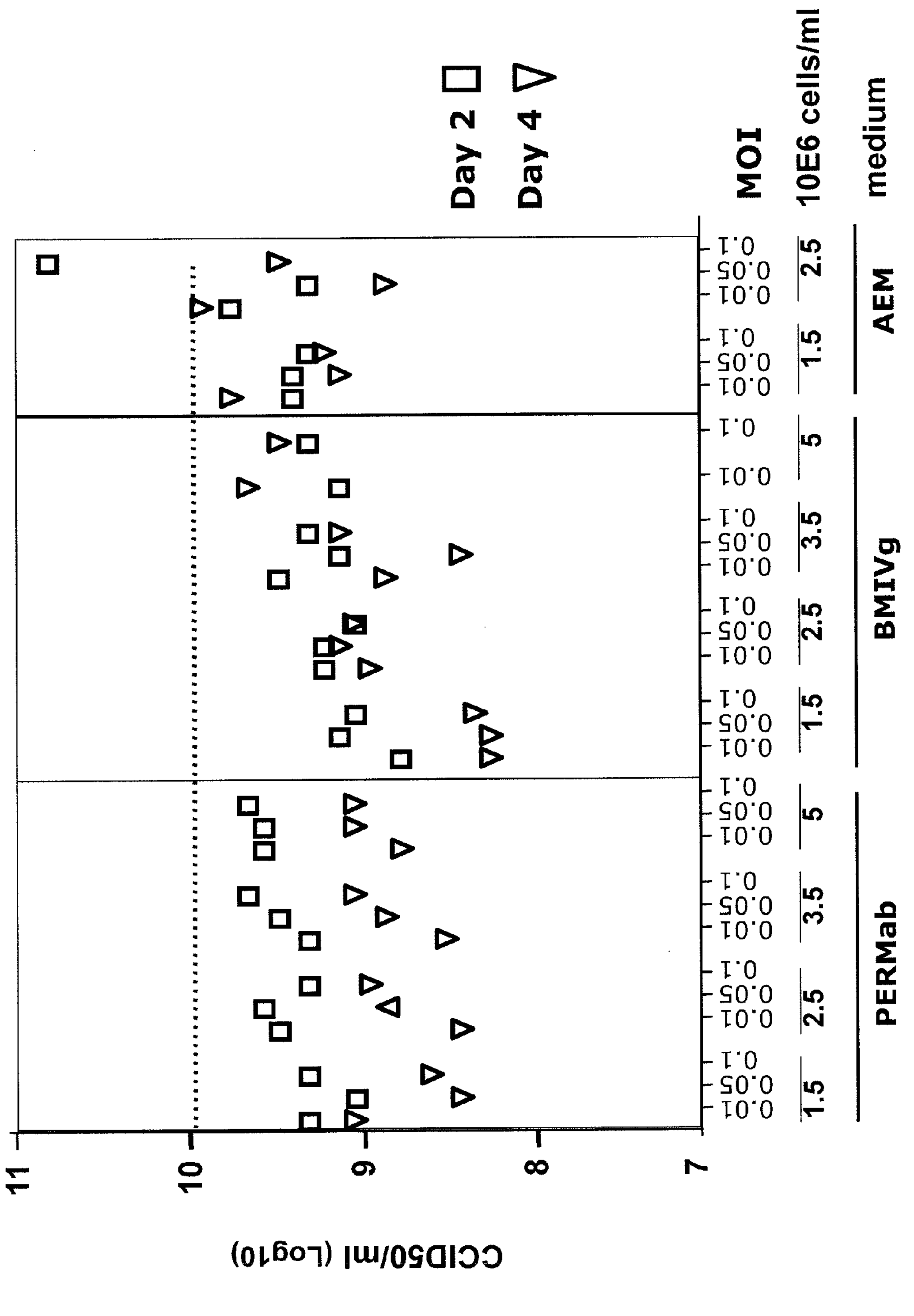
FIG. 2. Production of poliovirus type 1 in suspension PER.C6® cells in different serum-free media, at different MOIs and at different cell densities at infection.

FIG. 2 depicts the results of titration of these samples for day 2 and day 4 samples (day 3 data not shown). PER.C6® cells grown and infected in all three media were able to produce high titers of poliovirus type 1, although BMIVg medium gave somewhat lower titers compared to PERMAb and AEM medium. Furthermore, longer incubation did not result in higher titers. In contrast, the day 2 harvest gave in most cases higher titers compared to day 3 and 4 harvests. A consistent effect of the variation of the MOIs could not be seen in this experiment. Importantly, the use of higher cell densities at infection did result in higher volumetric titers showing that a suspension culture process using high cell densities is beneficial for the yield of infectious poliovirus.

Figure 3:
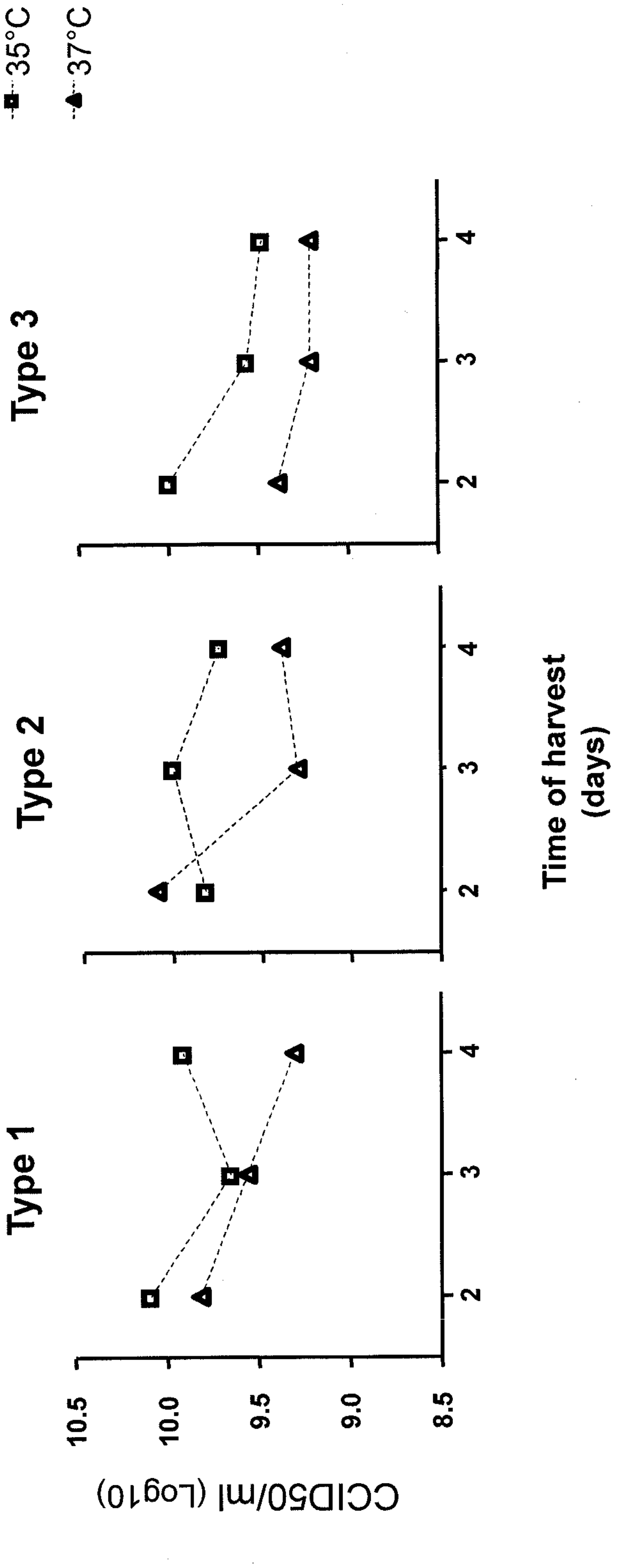
FIG. 3. Effect of temperature and time of harvest on production of poliovirus types 1, 2 and 3 in suspension PER.C6® cells in serum-free medium.

In a next experiment, the time of harvest and temperature during infection was compared for all three poliovirus strains. Hereto, PER.C6® cells were seeded in AEM medium at $2.5 \times 10^6$ cells/ml in 15 ml volumes in shaker flasks and infected with an MOI of 0.1 at 37° C. and at 35° C. of each poliovirus strain. Cells and medium were harvested 2, 3 and 4 days after infection and processed as described above. Analysis of the virus production under the different conditions was done by determination of $CCID_{50}$ values as described above and showed an increase in yield at 35° C. compared to 37° C. for all three types of poliovirus (FIG. 3). In addition it was confirmed and extended to poliovirus type 2 and 3 that in most cases the highest titers were measured when harvests were taken at day 2.

Example 3

Yield of Poliovirus on Suspension PER.C6® Cells Increases at Higher Cell Density To study if a further increase in cell density leads to an increase in virus titer, productions with $2.5 \times 10^6$ cells/ml were compared to $10 \times 10^6$ cells/ml. Hereto, PER.C6® cells in PERMAb medium were seeded in 15 ml volume in shake flasks at the indicated cell densities and infected with 2 CCID50/cell of poliovirus type 1 in triplicate. After 24 and 48 hours cells and medium were harvested and cleared lysates were prepared by freeze/thawing and centrifugation as described above. In addition to the previously tested temperatures 35 and 37° C., the experiment was also carried out at 33° C.

Figure 4:
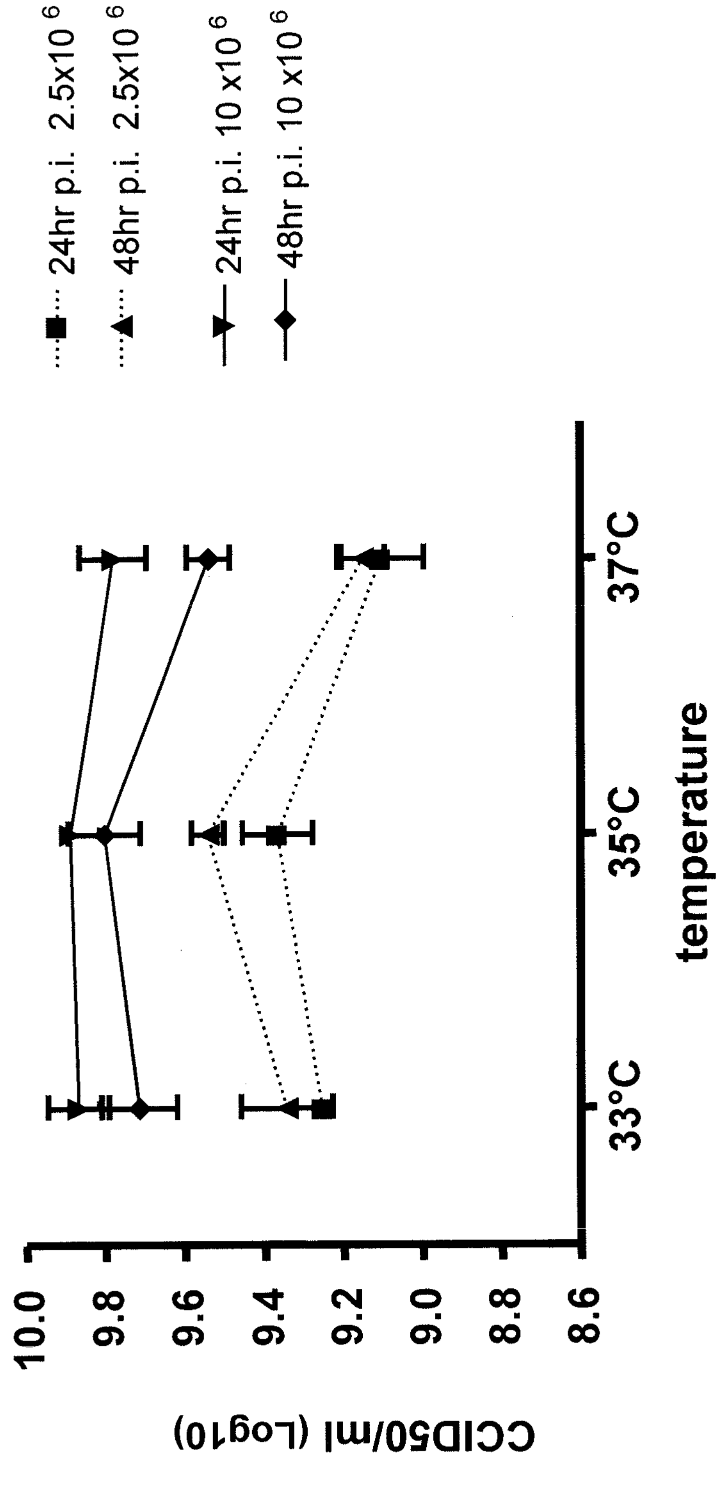
FIG. 4. Effect of cell density at infection, temperature, and time of harvest on production of poliovirus type 1 in suspension PER.C6® cells in serum-free medium.

Analysis of the titers by $CCID_{50}$ assay (FIG. 4) confirmed that the yield was improved when cells were infected at density of $10 \times 10^6$ cells/ml compared to $2.5 \times 10^6$ cells/ml. Best titers were obtained at 35° C. irrespective of cell density or harvest day. Furthermore, and indicative for the efficient propagation of poliovirus on PER.C6® cells, it was shown that harvests can also be taken after 24 hours since the yield in the 24 hours or 48 hours samples were quite comparable.

Figure 5:
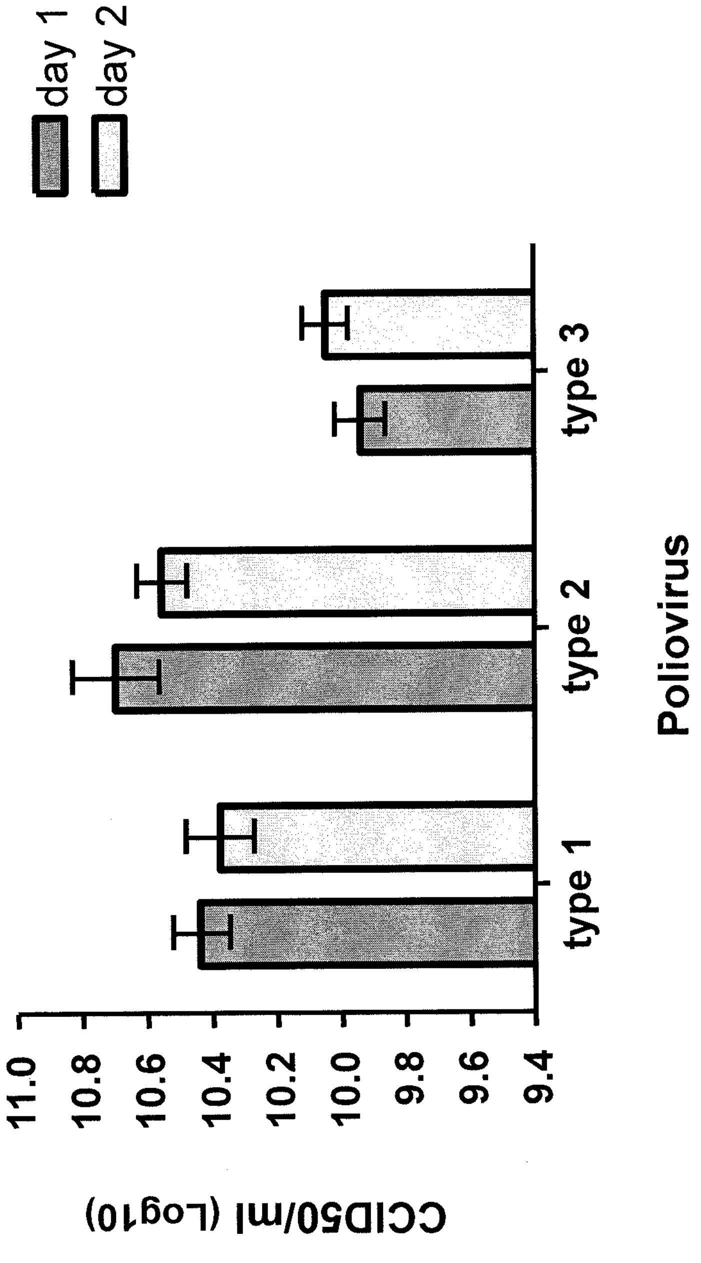
FIG. 5. Efficient production of poliovirus types 1, 2 and 3 in serum-free suspension PER.C6® cells at high cell densities.

In a next experiment, these conditions were tested also for the other types of poliovirus. PER.C6® cells were seeded in PERMAb medium at $10 \times 10^6$ cells/ml and infected with 2 CCID50/cell at 35° C. in shake flasks in triplicate with the different stocks of poliovirus. Harvests were done after 24 and 48 hours and cells and medium were processed to cleared lysates as described above. Titration by $CCID_{50}$ assay showed that the use of high cell densities also resulted in high yields of virus for type 2 and 3 (FIG. 5).

This clearly shows that high density cultures of PER.C6® cells in suspension provide an excellent platform for the production of wild type poliovirus. Since the cell density of the PER.C6® cells and size/volumes of the culture can be increased by using bioreactor systems, wave bags or other types of up-scalable systems for culturing, the production of poliovirus can be improved significantly compared to the current micro-carrier system with Vero cell cultures.

Produced poliovirus is harvested and purified according to methods known in the art and used for poliovirus propagated on Vero-cells, inactivated by formalin according to known methods, and subsequently the immunogenicity is tested using a standard rat immunogenicity assay, according to methods well known in the art (e.g., Bevilacqua et al., 1996). It is expected that the poliovirus thus produced has an immunogenicity comparable to poliovirus produced with conventional processes using Vero cells.

Example 4

Production of Poliovirus in PER.C6® Cells in a Bioreactor

Cells are thawed from a PER.C6® working cell bank, and propagated in serum free culture medium in a humidified incubator at 37° C. and 10% $CO_2$. Subculture is performed every 3 to 4 days until sufficient cell density is reached to inoculate a 2 L bioreactor at a cell density of $0.2\text{-}0.4 \times 10^6$ cells/mL. Cells are propagated in the 2 L bioreactor at 37° C., DO of 40%, and a pH of 7.3. When a cell density of approximately $2 \times 10^6$ cells/mL is reached (day 4 post inoculation) an ATF system is started, to allow the cells to be cultured for a longer period of time and to reach high cell densities. After approximately 11 to 12 days a cell density in the 2 L bioreactor is reached of more than $50 \times 10^6$ cells/mL. At this moment the cell suspension is transferred to a 10 L bioreactor. The cell suspension from the 2 L bioreactor is diluted 1:5 with serum free culture medium. The cell density in the 10 L bioreactor is between 10 and $15 \times 10^6$ cells/mL. Subsequently the 10 L bioreactor is infected with a poliovirus seed stock at an MOI of 2 $CCID_{50}$/cell. The production of poliovirus is performed at 35° C., pH 7.3 and DO of 40%. The 10 L bioreactor is sampled at certain time points for cell count and poliovirus production, and harvest of the poliovirus is suitably performed between 12 and 48 hours post infection.

REFERENCES

Barrett P N, Mundt W, Kistner O, Howard M K. 2009. Vero cell platform in vaccine production: moving towards cell culture-based viral vaccines. Expert Rev. Vaccines 8: 607-618.

Bevilacqua J M, Young L, Chiu S W, Sparkes J D, Kreeftenberg J G. 1996. Rat immunogenicity assay of inactivated poliovirus. Dev. Biol. Stand. 86: 121-127.

Byrd P, Brown K W, Gallimore P H. 1982. Malignant transformation of human embryo retinoblasts by cloned adenovirus 12 DNA. Nature 298: 69-71.

Byrd P J, Grand R J A, Gallimore P H. 1988. Differential transformation of primary human embryo retinal cells by adenovirus E1 regions and combinations of E1A+ras. Oncogene 2: 477-484.

Campbell S A, Lin J, Dobrikova E Y, Gromeier M. 2005. Genetic determinants of cell type-specific poliovirus propagation in HEK 293 cells. J. Virol. 79: 6281-6290.

Card C J, Smith T, Hunsaker B, Barnett B. 2005. Serum-free production of poliovirus: A comparative study using microcarriers, roller bottles and stationary cell culture. In: F. Gòdia and M. Fussenegger (Eds.), Animal Cell Technology meets Genomics, 761-765.

Doi Y, Abe S, Yamamoto H, Horie H, et al. 2001. Progress with inactivated poliovirus vaccines derived from the Sabin strains. In: Brown F (ed): Progress in Polio Eradication: Vaccine Strategies for the End Game. Dev. Biol. 105: 163-169.

Van Eikenhorst G, Bakker W A M, Thomassen Y E, van der Pol L A. 2009. Platform technology for viral vaccine production: comparison between attached and suspension Vero cells. Poster and Abstract P70. In: $21^{st}$ Meeting of the European Society for Animal Cell Technology, Programme and Book of Abstracts.

Fallaux F J, Bout A, van der Velde I, van den Wollenberg D J, Hehir K M, Keegan J, et al. New helper cells and matched early region 1-deleted adenovirus vectors prevent generation of replication-competent adenoviruses. Hum. Gene Ther. 1998 Sep. 1; 9(13):1909-17.

Furey J. Scale-up of a cell culture perfusion process—A low-shear filtration system that inhibits filter-membrane fouling. Genetic Engineering News. Vol. 22, No. 7, April 2002.

Gallimore, P. H., Grand, R. J. A. and Byrd, P. J. (1986). Transformation of human embryo retinoblasts with simian virus 40, adenovirus and ras oncogenes. AntiCancer Res. 6, p 499-508.

Jiang S, Pye D, Cox J C. 1986. Inactivation of poliovirus with β-propiolactone. J. Biol. Stand. 14: 103-109.

John J. 2009. Role of injectable and oral polio vaccines in polio eradication. Expert Rev. Vaccines 8: 5-8.

Kew O M, Sutter R W, de Gourville E M, Dowdle W R, Pallansch M A. 2005. Vaccine-derived polioviruses and the endgame strategy for global polio eradication. Annu. Rev. Microbiol. 59: 587-635.

Kral K M, Golden K, Zijlstra G, Swaying J, Nieboer M, Chon J H. 2009. Advances in high yielding platform production processes using the PER.C6® human cell line. Abstract P142. In: 21$^{st}$ Meeting of the European Society for Animal Cell Technology, Programme and Book of Abstracts.

Merten O.-W., Wu R, Couvé E, Crainic R. 1997. Evaluation of the serum-free medium MDSS2 for the production of poliovirus on Vero cells in bioreactors. Cytotechnology 25: 35-44.

Montagnon B, Vincent-Falquet J C, Fanget B. 1982. Thousand liter scale microcarrier culture of Vero cells for killed poliovirus vaccine. Promising results. Develop. Biol. Standard. 55: 37-42.

Montagnon B J, Fanget B, Vincent-Falquet J C. 1984. Industrial-scale production of inactivated poliovirus vaccine prepared by culture of Vero cells on microcarrier. Rev. Infect. Dis. 6 (suppl. 2): S341-S344.

Pau M G, Ophorst C, Koldijk M H, Schouten G, Mehtali M, Uytdehaag F. The human cell line PER.C6® provides a new manufacturing system for the production of influenza vaccines. Vaccine 2001 Mar. 21; 19(17-19):2716-21.

Van Wezel A L, van Steenis G, Hannik C A, Cohen H. 1978. New approach to the production of concentrated and purified inactivated polio and rabies tissue culture vaccines. Develop. biol. Standard. 41: 159-168.

Wright P F, Modlin J F. 2008. The demise and rebirth of Polio—A modern Phoenix? J. Infect. Dis. 197: 335-336.

Yakovenko M L, Korotkova E A, Ivanova O E, Eremeeva T P et al. 2009. Evolution of the Sabin vaccine into pathogenic derivatives without appreciable changes in antigenic properties: need for improvement of current poliovirus surveillance. J. Virol. 83: 3402-3406.

Yallop C, Crowley J, Cote J, Hegmans-Brouwer K, Lagerwerf F, Gagne R, Martin J C, Oosterhuis N, Opstelten D J, Bout A. PER.C6® cells for the manufacture of biopharmaceutical proteins. Modern Biopharmaceuticals—Design, Development and Optimization. Vol. 3, 2005.

What is claimed is:

1. A process for producing poliovirus, the process comprising:

providing a serum-free suspension culture of human fetal retina (HER) cells that have been immortalized by expression of adenovirus E1 sequences, infecting cells in the culture with poliovirus at a cell density of between $5\times10^6$ cells/mL and $50\times10^6$ cells/mL, and harvesting poliovirus at a time of between 12 and 48 hours after infection when the poliovirus in the culture has a titer of at least about $10^{9.4}$ $CCID_{50}$/mL.

2. The process of claim 1, comprising harvesting poliovirus at a titer of at least about $10^{9.8}$ $CCID_{50}$/mL.

3. The process of claim 1, comprising harvesting poliovirus at a titer of at least about $10^{10}$ $CCID_{50}$/mL.

4. The process of claim 1, wherein the poliovirus comprises poliovirus type 1, poliovirus type 2, or poliovirus type 3.

5. The process of claim 1, wherein the poliovirus is a wild-type poliovirus.

6. The process of claim 1, wherein the poliovirus is attenuated.

7. The process of claim 6, wherein the poliovirus is a Sabin strain.

8. The process of claim 1, wherein the process is conducted in a bioreactor.

9. The process of claim 8, wherein the bioreactor has a volume of between 1 and 1000 liters.

10. The process of claim 1, wherein the cells are infected with poliovirus at a multiplicity of infection of between 0.1 and 3 $CCID_{50}$/cell.

11. The process of claim 1, wherein the cells are infected at a cell density of between $8\times10^6$ cells/ml and $50\times10^6$ cells/mL.

12. The process of claim 1, wherein the cells are infected at a cell density of between $20\times10^6$ cells/ml and $50\times10^6$ cells/mL.

13. The process of claim 1, comprising culturing the cells at a temperature of between 34° C. and 36° C.

14. The process of claim 1, wherein the cells are as deposited with the European Collection of Cell Cultures (ECACC), under deposit reference number 96022940.

15. The process of claim 1, further comprising:

purifying and inactivating the harvested poliovirus.

16. The process of claim 15, further comprising formulating the inactivated poliovirus into a pharmaceutical composition.

17. A method for producing inactivated polio vaccine (IPV) composition, the method comprising:

(i) obtaining a poliovirus preparation in cell culture at a titer of at least about $10^{9.4}$ $CCID_{50}$/ml by a process comprising:

a) providing a serum-free suspension culture of cells, which are HER cells that have been immortalized by expression of adenovirus E1 sequences, b) infecting cells in the culture with poliovirus, at a cell density of between $5\times10^6$ cells/ml and $50\times10^6$ cells/ml, and c) harvesting poliovirus at a time of between 12 and 48 hours after infection to obtain the poliovirus preparation having a titer of at least about $10^{9.4}$ $CCID_{50}$/ml;

(ii) purifying and inactivating the harvested poliovirus;

(iii) formulating the inactivated poliovirus to obtain an IPV composition.

18. The method of claim 17, wherein in step (i) c), the poliovirus is harvested at a titer of at least about $10^{9.8}$ $CCID_{50}$/mL.

19. The method of claim 17, wherein in step (i) c), the poliovirus is harvested at a titer of at least about $10^{10}$ $CCID_{50}$/mL.

20. The method of claim 17, wherein the cells are as deposited with the European Collection of Cell Cultures (ECACC), under deposit reference number 96022940.

21. The method of claim 17, wherein in step (i) b), the cells are infected at a cell density of between $8\times10^6$ cells/ml and $50\times10^6$ cells/ml.

22. The method of claim 17, wherein in step (i) b), the cells are infected at a cell density of between $20\times10^6$ cells/ml and $50\times10^6$ cells/ml.

23. The method of claim 17, comprising culturing the cells at a temperature of between 34° C. and 36° C.

24. The method of claim 17, wherein the poliovirus is a poliovirus type 1, poliovirus type 2, or poliovirus type 3.

25. The method of claim 17, wherein the poliovirus is a wild-type poliovirus.

26. The method of claim 17, wherein the poliovirus is attenuated.

27. The method of claim 26, wherein the poliovirus is a Sabin strain.

28. The method of claim 17, wherein in step (i) b), the cells are infected with poliovirus at a multiplicity of infection of between 0.1 and 3 $CCID_{50}$/cell.

29. A process for producing a poliovirus bulk useful for preparing a polio vaccine, the process comprising:

infecting a serum-free suspension culture of HER cells that have been immortalized by expression of adenovirus E1 sequences with poliovirus at a cell density of between $5\times10^6$ cells/ml and $50\times10^6$ cells/ml; and harvesting poliovirus at a time of between 12 and 48 hours after infection to obtain the poliovirus bulk comprising culture medium and poliovirus at a titer of at least about $10^{9.4}$ $CCID_{50}$/mL.

30. The process of claim 29, wherein the poliovirus bulk comprises culture medium and poliovirus at a titer of at least about $10^{9.8}$ $CCID_{50}$/mL.

31. The process of claim 29, wherein the poliovirus bulk comprises culture medium and poliovirus at a titer of at least about $10^{10}$ $CCID_{50}$/mL.

32. A method for preparing a trivalent IPV composition, the method comprising:

(A) (i) obtaining a type 1 poliovirus preparation in cell culture at a titer of at least about $10^{9.4}$ $CCID_{50}$/ml by a process comprising:

a) providing a serum-free suspension culture of cells, which are HER cells that have been immortalized by expression of adenovirus E1 sequences, b) infecting cells in the culture with type 1 poliovirus, at a cell density of between $5\times10^6$ cells/ml and $50\times10^6$ cells/ml, and c) harvesting type 1 poliovirus at a time of between 12 and 48 hours after infection to obtain the type 1 poliovirus preparation having a titer of at least about $10^{9.4}$ $CCID_{50}$/ml;

(ii) purifying and inactivating the harvested type 1 poliovirus to obtain an inactivated type 1 poliovirus;

(B) (i) obtaining a type 2 poliovirus preparation in cell culture at a titer of at least about $10^{9.4}$ $CCID_{50}$/ml by a process comprising:

a) providing a serum-free suspension culture of cells, which are HER cells that have been immortalized by expression of adenovirus E1 sequences, b) infecting cells in the culture with type 2 poliovirus, at a cell density of between $5\times10^6$ cells/ml and $50\times10^6$ cells/ml, and c) harvesting type 2 poliovirus at a time of between 12 and 48 hours after infection to obtain the type 2 poliovirus preparation having a titer of at least about $10^{9.4}$ $CCID_{50}$/ml;

(ii) purifying and inactivating the harvested type 2 poliovirus to obtain an inactivated type 2 poliovirus;

(C) (i) obtaining a type 3 poliovirus preparation in cell culture at a titer of at least about $10^{9.4}$ $CCID_{50}$/ml by a process comprising:

a) providing a serum-free suspension culture of cells, which are HER cells that have been immortalized by expression of adenovirus E1 sequences, b) infecting cells in the culture with type 3 poliovirus, at a cell density of between $5\times10^6$ cells/ml and $50\times10^6$ cells/ml, and c) harvesting type 3 poliovirus at a time of between 12 and 48 hours after infection to obtain the type 3 poliovirus preparation having a titer of at least about $10^{9.4}$ $CCID_{50}$/ml;

(ii) purifying and inactivating the harvested type 3 poliovirus to obtain an inactivated type 3 poliovirus; and (D) mixing the inactivated type 1 poliovirus, inactivated type 2 poliovirus and inactivated type 3 poliovirus to obtain the trivalent IPV composition.

33. The method of claim 32, wherein the trivalent IPV composition per dose comprises about 40 D-antigen units (DU) of type 1 poliovirus, about 8 DU of type 2 poliovirus and about 32 DU of type 3 poliovirus.

* * * * *